United States Patent
Langanke et al.

(10) Patent No.: US 11,788,107 B2
(45) Date of Patent: Oct. 17, 2023

(54) METHOD FOR PRODUCING ANILINE OR AN ANILINE DERIVATIVE

(71) Applicant: Covestro Intellectual Property Gmbh & Co. Kg, Leverkusen (DE)

(72) Inventors: Jens Langanke, Mechernich (DE); Franz Beggel, Cologne (DE); Gernot Jaeger, Cologne (DE); Wolf Kloeckner, Cologne (DE); Volker Michele, Cologne (DE); Thomas Voessing, Düsseldorf (DE)

(73) Assignee: Covestro Intellectual Property Gmbh & Co. Kg, Leverkusen (DE)

( * ) Notice: Subject to any disclaimer, the term of this patent is extended or adjusted under 35 U.S.C. 154(b) by 495 days.

(21) Appl. No.: 17/262,269

(22) PCT Filed: Jul. 24, 2019

(86) PCT No.: PCT/EP2019/069859
§ 371 (c)(1),
(2) Date: Jan. 22, 2021

(87) PCT Pub. No.: WO2020/020919
PCT Pub. Date: Jan. 30, 2020

(65) Prior Publication Data
US 2021/0238638 A1    Aug. 5, 2021

(30) Foreign Application Priority Data
Jul. 27, 2018   (EP) .................................... 18186072

(51) Int. Cl.
C12P 13/00    (2006.01)
C07C 209/68   (2006.01)
C09B 29/01    (2006.01)

(52) U.S. Cl.
CPC .......... C12P 13/001 (2013.01); C07C 209/68 (2013.01); C09B 29/0003 (2013.01)

(58) Field of Classification Search
CPC .................................................. C12P 13/001
See application file for complete search history.

(56) References Cited

U.S. PATENT DOCUMENTS

| 4,233,459 A | 11/1980 | Kilpper et al. |
| 4,328,339 A | 5/1982 | Kilpper et al. |
| 4,851,570 A | 7/1989 | Zaby et al. |
| 5,053,539 A | 10/1991 | Yano et al. |
| 5,145,958 A | 9/1992 | Kissener et al. |
| 5,286,760 A | 2/1994 | Bolton et al. |
| 7,230,130 B2 | 6/2007 | Strofer et al. |
| 7,253,321 B2 | 8/2007 | Hagen et al. |
| 7,547,801 B2 | 6/2009 | Pohl et al. |
| 7,692,042 B2 | 4/2010 | Dugal et al. |
| 8,079,752 B2 | 12/2011 | Rausch et al. |
| 8,097,751 B2 | 1/2012 | Koch et al. |
| 8,455,691 B2 | 6/2013 | Sommer et al. |
| 10,173,969 B2 | 1/2019 | Jaeger et al. |
| 10,731,187 B2 | 8/2020 | Jaeger et al. |
| 2007/0238901 A1 | 10/2007 | Dugal et al. |
| 2010/0324336 A1 | 12/2010 | Sommer et al. |
| 2018/0334694 A1 | 11/2018 | Jäger et al. |
| 2018/0371512 A1 | 12/2018 | Jäger et al. |
| 2019/0382812 A1 | 12/2019 | Jäger et al. |

FOREIGN PATENT DOCUMENTS

| JP | 2013230993 A | 11/2013 |
| JP | 2016222575 A | 12/2016 |
| WO | 2018002088 A1 | 1/2018 |
| WO | 2019234092 A1 | 12/2019 |

OTHER PUBLICATIONS

Wiklund et al., Current Organic Synthesis, 2006, 3, 379-402.
Stevens et al., Canadian Journal of Chemistry, 1952, 30 (7), 529-540.
MacMaster and Shriner, J. Am. Chem. Soc., 1923, 45 (3), 751-753.
Balderas-Hernandez, V. E. et al., "Metabolic engineering for improving anthranilate synthesis from glusose in *Escherichia coli*", Microb. Cell. Fact. 2009, 8, 19 (doi: 10-118611475-2859-8-19).
Kamm et al., p-Nitrobenzoic acid in Organic Syntheses, vol. 1, 1941, pp. 392 ff.
Kamm et al., Methyl m-nitrobenzoate in Organic Syntheses, vol. 1, 1941, pp. 372 ff.
Kamm et al., m-Nitrobenzoic acid in Organic Syntheses, vol. 1, 1941, pp. 391 ff.
International Search Report, PCT/EP2019/069859, dated Oct. 17, 2019, Authorized officer: Benigno Megido.

*Primary Examiner* — Golam M Shameem
(74) *Attorney, Agent, or Firm* — Donald R. Palladino

(57) ABSTRACT

The invention relates to a method for producing aniline or an aniline derivative, in which a solution of aminobenzoic acid in aniline with a mass fraction of aniline in the solution, in relation to the total mass of aminobenzoic acid and aniline, in the region of 20% to 85%, is subject to a thermal decarboxylation at a temperature in the region of 165° C. to 500° C. without the presence of a non-system catalyst, such that the aminobenzoic acid is converted into aniline. The obtained aniline can be converted into derivatives, such as di- and polyamines of the diphenylmethane series.

14 Claims, No Drawings

METHOD FOR PRODUCING ANILINE OR AN ANILINE DERIVATIVE

CROSS-REFERENCE TO RELATED APPLICATION

This application is a national stage application under 35 U.S.C. § 371 of PCT/EP2019/069859, filed Jul. 24, 2019, which claims the benefit of European Application No. 18186072.7, filed Jul. 27, 2018, each of which is incorporated herein by reference.

FIELD

The present invention relates to a process for preparing aniline or an aniline conversion product, in which a solution of aminobenzoic acid in aniline having a proportion by mass of aniline in the solution based on the total mass of aminobenzoic acid and aniline in the range from 20% to 85% is subjected to a thermal decarboxylation at a temperature in the range from 165° C. to 500° C. without the presence of a catalyst extraneous to the system, such that the aminobenzoic acid is converted to aniline. The resultant aniline can be converted to conversion products, for example the di- and polyamines of the diphenylmethane series.

BACKGROUND

The preparation of aniline by decarboxylation of aminobenzoic acid is known in principle in the prior art; see for example Per Wiklund et al., *Current Organic Synthesis*, 2006, 3, 379-402. Stevens et al., *Canadian Journal of Chemistry*, 1952, 30 (7), 529-540, reports that it was possible to decarboxylate an aqueous solution of ortho-aminobenzoic acid to aniline in the presence of 0.75 N sulfuric acid at 100° C. in 6 hours with a 56% yield. It had previously been reported in MacMaster and Shriner, *J. Am. Chem. Soc.*, 1923, 45 (3), 751-753 that, under similar conditions (in boiling water) but in the absence of acid, ortho-aminobenzoic acid was decarboxylated to aniline in 7 hours with only a 27% yield.

There are also publications in this regard in the recent patent literature; in this regard see, in particular, international publications WO 2015/124686 A1 and WO 2015/124687 A1:

WO 2015/124686 A1 describes the decarboxylation of the anion of anthranilic acid, ortho-aminobenzoate, especially in the form of the ammonium salt ammonium ortho-aminobenzoate, in the presence of a catalyst or without catalyst in aqueous medium, wherein the ortho-aminobenzoate is preferably obtained by fermentation. The approach described in WO 2015/124686 A1 of directly decarboxylating an aqueous solution of ortho-aminobenzoate provided by fermentation, optionally after removal of biomass, is certainly not unattractive per se. However, the process described in WO 2015/124686 A1 entails the extraction of aniline formed in the decarboxylation with an organic solvent extraneous to the system (an alcohol, phenol, amide, ether or aromatic hydrocarbon; in particular, 1-dodecanol is emphasized as a suitable solvent), which is inevitably associated with additional costs and additional purification complexity (separation of aniline from 1-dodecanol). Furthermore, the entire fermentation broth containing a significant proportion of water (typically >80% by mass) has to be heated up in order to initiate the decarboxylation to give aniline, which is inevitably associated with high energy costs.

WO 2015/124687 A1 describes the catalytic decarboxylation of anthranilic acid (ortho-aminobenzoic acid) under the action of zeolite catalysts in 1-decanol as solvent. WO 2015/124687 A1 describes the performance of the decarboxylation in solvents including water or in an organic solvent extraneous to the system, especially 1-dodecanol, optionally in the mixture with aniline (cf. page 18, lines 28 and 29). The disadvantages outlined above of using an organic solvent extraneous to the system are therefore also relevant to these embodiments of the decarboxylation. In addition, this document also describes the option of performing the decarboxylation in aniline (without 1-dodecanol; see FIGS. 35 and 37 to 38 and the accompanying text passages), optionally in the presence of 10% by mass of water (see FIG. 36 and the accompanying text passages). The description of this process variant does not go beyond the indication of the option in principle of such a decarboxylation of aminobenzoic acid from different sources of aniline. Decarboxylation in aniline without a further catalyst at a temperature of 160° C. has been described as unsuccessful (only negligible conversions).

Both applications further describe the further conversion of the aniline thus prepared to aniline conversion products such as di- and polyamines of the diphenylmethane series and the corresponding isocyanates.

Japanese patent application JP 2016/222575 describes a process for obtaining an anti-aging agent or vulcanization accelerator by hydrolyzing indigo, which is obtained in turn by extraction of plants, using 2-aminobenzoic acid, decarboxylating the 2-aminobenzoic acid to aniline and then further converting the aniline thus formed. The decarboxylation step can be performed in the presence of an acid such as acetic acid or sulfuric acid or else without such acids. In the example, the decarboxylation is effected without adding acids or other compounds in a nitrogen atmosphere at 190° C. and ambient pressure.

International patent application WO 2017/085170 A1 describes a preferred configuration of the isolation of aminobenzoic acid obtained by fermentation from the resultant fermentation broth by crystallization. Likewise described is the option of converting the aminobenzoic acid thus isolated to aniline by decarboxylation. No autocatalytic effect of the aniline formed in the decarboxylation that could make it possible to dispense with an additional catalyst in an industrial scale process can be inferred from this document.

International patent application WO 2018/002088 A1 describes the decarboxylation of aminobenzoic acid to aniline in the presence of a catalyst, especially a zeolite, wherein a portion of the crude aniline formed is recycled and used as solvent.

As yet unpublished international patent application PCT/EP2017/083374 with application number is concerned with the step of isolating aminobenzoic acid from an aqueous fermentation solution using adsorption and desorption steps. No autocatalytic effect of the aniline formed in the decarboxylation that could make it possible to dispense with an additional catalyst in an industrial scale process can be inferred from this document.

Japanese patent application JP 2013-230993 describes the decarboxylation of para- and ortho-aminobenzoic acid in the molten state or in aqueous or alcoholic solution without catalyst at pressures in the range from ambient pressure to 1.0 MPa$_{(ü)}$. It is recommended that the aniline formed be removed continuously because it would otherwise inhibit the reaction. For instance, comparative example 1 reports that the reaction of para-aminobenzoic acid in aniline at an aniline content of 89% by mass at 200° C. after the reaction time of 3 hours resulted to 11.1% conversion and 2.9% yield.

American patent U.S. Pat. No. 5,145,958 describes a process for preparing 2,4- or 2,6-dihaloaniline by reacting an aminobenzoic ester with a chlorinating or brominating agent in an organic solvent such as, in particular, chlorobenzene, dichlorobenzene, carbon tetrachloride or bromobenzene, followed by hydrolysis and decarboxylation in water or in a water-containing solvent or diluent such as, in particular, toluene, chlorobenzene, acetic acid, hydrochloric acid or sulfuric acid. There is no description of the preparation of (non-halogen-substituted) aniline.

The aminobenzoic acid starting compound required for the preparation of aniline by decarboxylation (as well as processes ultimately based on the extraction of plants, as described above in connection with the discussion of JP 2016/222575) may be prepared chemically or—preferably within the scope of the present invention—by fermentation.

The chemical preparation of aminobenzoic acid is described in the literature. A suitable synthesis route (with yields >98%) is, for example, the reaction of phthalimide with sodium hypochlorite. Phthalimide can itself be obtained from phthalic anhydride and ammonia. The whole process is well-known and is described, for example, in Lorz et al., *Phthalic Acid and Derivatives* in Ullmann's Encyclopedia of Industrial Chemistry, Volume 27, pp. 140-141, Weinheim, Wiley-VCH. An industrial process is likewise described in the patent literature; see, for example, DE 29 02 978 A1 and EP 0 004 635 A2.

Fermentative preparation of aminobenzoic acid is described in the literature. For the fermentative preparation of aminobenzoic acid, reference is made by way of example to Balderas-Hemandez, V. E. et al., "Metabolic engineering for improving anthranilate synthesis from glucose in *Escherichia coli*", Microb. Cell. Fact. 2009, 8, 19 (doi: 10.118611475-2859-8-19). The patent literature also includes publications in this regard; see, for example, the applications WO 2015/124686 A1 and WO 2015/124687 A1 mentioned at the outset and the literature cited in each. Fermentation processes proceed in an aqueous environment and, in the case of preparation of aminobenzoic acid, generally afford aqueous solutions (fermentation broths) with a content by mass of aminobenzoic acid (if appropriate in the form of the anion) in the range from 10.0 g/L to 100 g/L.

There are currently no "bio-based processes" (for the purposes of the present invention: preparation processes based on renewable raw materials employing fermentative processes) for preparation of aminobenzoic acid or aniline that are performed commercially and on a large production scale. Consequently—on the industrial scale—no subsequent synthesis based on bio-based aminobenzoic acid or based on bio-based aniline is possible either.

DETAILED DESCRIPTION

Further improvements in the preparation of aniline and aniline conversion products by decarboxylation of aminobenzoic acid, especially obtained by fermentation, would therefore be desirable. More particularly, it would be desirable to be able to perform the process in a very simple manner and without the use of catalysts extraneous to the system, in order to increase the economic viability of the process. This is desirable especially since the heterogeneous zeolite catalysts that are described as preferred in the literature not only constitute a not inconsiderable cost factor but also bring process-related restrictions even when used on the industrial production scale. Particular examples include the following challenges: selection and operation of specific reactors for a heterogeneously catalyzed process, introduction of the catalyst into the process, including the shaping of the catalyst particles, retention of the catalyst, mass transfer limitations resulting from the heterogeneous catalyst, fouling of the catalyst, deactivation of the catalyst over time (catalyst service life), removal of the deactivated catalyst (for example "deinstallation" during shutdown times), purifying and regeneration of the heterogeneous catalyst— especially outside the reactor—and finally disposal of no longer adequately regeneratable catalyst. Therefore, the possibility of dispensing with such catalysts would make the process more favorable overall not just with regard to capital costs (absence of catalyst costs), but would also enable more reliable operation of the process associated with a reduced risk of shutdown time, and would lead to a technically much simpler process and hence make the use thereof more attractive on the industrial production scale. The absence of a heterogeneous catalyst extraneous to the system also results in further degrees of freedom in the technical execution of the decarboxylation reactor; for instance, it is not necessary to provide a concept for retention of the catalyst. Comparable arguments can be made for homogeneous catalysts extraneous to the system. As well as the not inconsiderable catalyst costs, the use thereof on the industrial production scale is also associated with process-related challenges. Particular examples include the following: introduction of the catalyst into the reaction apparatus, retention in continuous mode and/or separation of the catalyst from the reaction mixture after the reaction (this is relevant both for the continuous and batchwise mode of operation), deactivation of the catalyst over time (catalyst service life), withdrawal by removal of the deactivated catalyst, regeneration of the homogeneous catalyst in an additional process step and/or additional apparatus(es) and finally disposal of no longer sufficiently regeneratable or irreversibly deactivated catalyst. The workup and regeneration of homogeneous catalysts is generally difficult and/or complex, and impossible or uneconomic in many cases.

Taking account of the above, the present invention provides a process for preparing aniline or an aniline conversion product, comprising the following steps:

(I) providing a solution of aminobenzoic acid, especially ortho-aminobenzoic acid, in aniline, with establishment of a proportion by mass of aniline in the solution based on the total mass of aminobenzoic acid and aniline of 20% to 85%, preferably 40% to 80%, more preferably 50% to 75%;

(II) converting aminobenzoic acid containing in the solution provided in step (I) to aniline in a reactor by thermally decarboxylating at a temperature in the range from 165° C. to 500° C. without the presence of any catalyst extraneous to the system;

(III) optionally converting aniline obtained in step (II) to an aniline conversion product.

It has been found that, completely surprisingly, the decarboxylation of aminobenzoic acid is possible even without using a catalyst extraneous to the system when the aminobenzoic acid is dissolved in aniline such that aniline is present in the abovementioned proportions in the resulting solution and the reaction is performed at sufficiently high temperature. This result is at odds with the results reported to date in the literature, which either say that the reaction does not proceed further satisfactorily without catalyst extraneous to the system (e.g. WO 2015/124687 A1) or which do report uncatalyzed reactions (JP 2013-230993), but these were conducted under conditions that are disadvantageous for other reasons (in the melt, which is difficult to control in terms of process technology, or in water, which, owing to the low water solubility of aminobenzoic acid, necessitates working with suspensions, which is undesirable for process technology reasons, and very energy-intensive isolation of the aniline product from the water used (for example by distillation), or in alcoholic solution, which necessitates the use of a solvent extraneous to the system).

Without wishing to be tied to a theory, it is suspected that aniline has autocatalytic action in the operating window of concentration and temperature mentioned, i.e. catalyzes its own further formation from the aminobenzoic acid present by decarboxylation. Therefore, the reaction, according to the invention, is performed "without the presence of a catalyst extraneous to the system". "Catalysts extraneous to the system" are the terminology of the present invention those catalysts that are not inherent to the process, i.e. are not automatically present in the process in any case or formed by the process. The requirement for absence of catalysts extraneous to the system should therefore be understood to mean that no further decarboxylation catalysts (for example the zeolites known from the literature) are added to the solution of aminobenzoic acid in aniline that is to be decarboxylated. The aniline present in the solution, by contrast, is regarded as a catalyst inherent to the process, since aniline is the product of the reaction.

According to the invention, the "proportion by mass of aniline" "in the solution provided in step (I)" is based on "the total mass of aminobenzoic acid and aniline", i.e. on the sum total of the masses of aminobenzoic acid and aniline excluding any further solvents present (such as, in particular, water, which is present in preferred embodiments as elucidated further down).

In the context of the present invention, the term "aniline conversion product" refers to a product which is obtained by further chemical conversion of aniline.

In the context of the present invention, pH values relate to 20° C.

There firstly follows a brief summary of various possible embodiments of the invention: In a first embodiment of the invention, which can be combined with all other embodiments, step (I) is performed by mixing aminobenzoic acid and aniline in a batchwise or continuous mixer.

In a second embodiment of the invention, which is a particular configuration of the first embodiment, the mixer used is a stirred tank.

In a third embodiment of the invention, which is a particular configuration of the first and second embodiments, the mixer from step (I) and the reactor from step (II) are operated continuously.

In a fourth embodiment of the invention, which is another particular configuration of the first and second embodiments, step (I) is performed using multiple, especially two, batchwise mixers connected in parallel and the reactor from step (II) is operated continuously, wherein, at any time in the continuous operation of the reactor from step (II), the solution of the aminobenzoic acid from one of the mixers used in step (I) is introduced into the reactor from step (II), while the mixing of the aminobenzoic acid into aniline is proceeding in another of these mixers.

In a fifth embodiment of the invention, which can be combined with all other embodiments, the thermal decarboxylating of the aminobenzoic acid is a first partial step (II)(1) of step (II), which is followed by a second partial step (II)(2) in which aniline formed in partial step (II)(1) is purified, especially by distillation in a distillation column.

In a sixth embodiment of the invention, which is a particular configuration of the fifth embodiment, the aniline used in step (I) is taken from the aniline formed in partial step (II)(1).

In a seventh embodiment of the invention, which is another particular configuration of the fifth embodiment, the aniline used in step (I) is taken from the aniline purified in partial step (I)(2).

In an eighth embodiment of the invention, which is another particular configuration of the fifth embodiment, the aniline used in step (I) is taken from the aniline formed in partial step (I)(1) and from the aniline purified in partial step (I)(2).

In a ninth embodiment of the invention, which is a particular configuration of the sixth and eighth embodiments, the aniline formed in partial step (II)(1) is divided into two streams in a mass ratio in the range from 9.0:1 to 1:9.0, one of which is supplied to the purification from partial step (I)(2) and the other used to provide the solution in step (I).

In a tenth embodiment of the invention, which can be combined with all other embodiments, in step (I), aminobenzoic acid is dissolved in aniline at a temperature in the range from −6° C. to 120° C., preferably 20° C. to 120° C., more preferably 30° C. to 120° C.

In an eleventh embodiment of the invention, which is a particular configuration of the tenth embodiment, aminobenzoic acid and aniline are first mixed at a temperature in the range from −6° C. to 100° C., preferably 20° C. to 100° C., more preferably 30° C. to 120° C., and then heated in an inert gas atmosphere to a temperature in the range from >100° C. to 120° C.

In a twelfth embodiment of the invention, which is a particular configuration of the tenth and eleventh embodiments, the temperature of the solution obtained in step (I) is increased to the temperature of step (II) by indirect heating in a heat exchanger, observing a dwell time of the solution from entry into the heat exchanger to entry into the reactor from step (II) in the range from 0.1 s to 120 s.

In a thirteenth embodiment of the invention, which is a particular configuration of the tenth, eleventh and twelfth embodiments, in step (I), aminobenzoic acid is dissolved in aniline at a pressure in the range from 0.90 $bar_{(abs.)}$ to 3.0 $bar_{(abs.)}$, preferably 1.0 $bar_{(abs.)}$ to 3.0 $bar_{(abs.)}$.

In a fourteenth embodiment of the invention, which can be combined with all other embodiments, the thermal decarboxylating in step (II) is performed at a temperature in the range from 185° C. to 450° C., preferably in the range from 205° C. to 425° C., more preferably in the range from 225° C. to 400° C., most preferably in the range from 255° C. to 375° C.

In a fifteenth embodiment of the invention, which can be combined with all other embodiments, the thermal decarboxylating in step (II) is performed at a pressure in the range from 4.0 $bar_{(abs.)}$ to 30 $bar_{(abs.)}$, preferably 5.0 $bar_{(abs.)}$ to 20 $bar_{(abs.)}$, more preferably 6.0 $bar_{(abs.)}$ to 10 $bar_{(abs.)}$ and most preferably 7.0 $bar_{(abs.)}$ to 9.0 $bar_{(abs.)}$.

In a sixteenth embodiment of the invention, which can be combined with all other embodiments, the reactor used in step (II) is a continuously operated tubular reactor or a bubble column reactor, preferably a bubble column reactor.

In a seventeenth embodiment of the invention, which is a particular configuration of the sixteenth embodiment, the reactor used in step (II) is a bubble column reactor, where the bubble column reactor has internals.

In an eighteenth embodiment of the invention, which is a particular configuration of the seventeenth embodiment, the internals are perforated trays by which the bubble column reactor is divided into compartments.

In a nineteenth embodiment of the invention, which is a particular configuration of the fifth embodiment and of all embodiments derived therefrom, a liquid, aniline-containing stream and a gaseous, carbon dioxide- and gaseous aniline-containing stream are taken from the reactor from step (II) continuously, wherein the gaseous stream passes through a condenser in which gaseous aniline is liquefied and from which carbon dioxide is discharged in gaseous form, wherein liquid aniline obtained in the condenser is fed to partial step (II)(1) and/or to partial step (II)(2).

In a twentieth embodiment of the invention, which is a particular configuration of the nineteenth embodiment, the pressure of the carbon dioxide discharged from the condenser in gaseous form is adjusted to a value in the range from 1.0 $bar_{(abs.)}$ to 30 $bar_{(abs.)}$, preferably 2.0 $bar_{(abs.)}$ to 20 $bar_{(abs.)}$, more preferably 3.0 $bar_{(abs.)}$ to 10 $bar_{(abs.)}$ and most preferably 3.0 $bar_{(abs.)}$ to 9.0 $bar_{(abs.)}$.

In a twenty-first embodiment of the invention, which can be combined with all other embodiments, the providing of the solution of aminobenzoic acid in aniline in step (I) comprises the chemical preparation of aminobenzoic acid.

In a twenty-second embodiment of the invention, which can be combined with all other embodiments to the extent that they do not relate to the purely chemical preparation of aminobenzoic acid, the providing of the solution of aminobenzoic acid in aniline in step (I) comprises the following partial steps:

(I)(1) fermenting a raw material comprising at least
  a fermentable carbon compound and
  a nitrogen compound,
    in a fermentation reactor using microorganisms to obtain an aminobenzoate- and/or aminobenzoic acid-containing fermentation broth,
    obtaining aminobenzoic acid from the fermentation broth;
and
(I)(2) dissolving the aminobenzoic acid obtained from the fermentation broth in step (I)(1) in aniline.

In a twenty-third embodiment of the invention, which is a particular configuration of the twenty-second embodiment, the obtaining of the aminobenzoic acid comprises a step of precipitating aminobenzoic acid by acid treatment, for which purpose the acid used comprises hydrochloric acid, sulfuric acid and/or phosphoric acid.

In a twenty-fourth embodiment of the invention, which is a particular configuration of the twenty-second embodiment and all embodiments derived therefrom, the fermenting is performed in the presence of a calcium salt, especially an inorganic calcium salt, such that calcium aminobenzoate is precipitated, wherein the obtaining of aminobenzoic acid from the fermentation broth comprises the following:

(i) converting calcium aminobenzoate to a water-soluble form by adding an aqueous phase containing water-soluble cations that form aminobenzoate salts (especially lithium, sodium, potassium and/or ammonium cations, preferably ammonium cations) and anions that form water-insoluble calcium salts (especially carbonate and/or hydrogen carbonate anions);
(ii) separating off an aqueous solution of aminobenzoate;
(iii) introducing carbon dioxide at a pressure of not less than 1.50 $bar_{(abs.)}$ into the aqueous solution of aminobenzoate separated off, so as to form a suspension containing aminobenzoic acid in an aqueous solution;
(iv) isolating the aminobenzoic acid separated out, comprising lowering the pressure with release of carbon dioxide to obtain a carbon dioxide-depleted aqueous solution that has been freed of aminobenzoic acid separated out;
(v) using the resultant aqueous solution that has been depleted of carbon dioxide and freed of aminobenzoic acid separated out as constituent, optionally sole constituent, of the aqueous phase added in step (i).

In a twenty-fifth embodiment of the invention, which is a particular configuration of the twenty-second embodiment and all embodiments derived therefrom, the fermentable carbon compound used in step (I)(1) comprises starch hydrolyzate, sugarcane juice, sugarbeet juice, hydrolyzates of lignocellulosic raw materials or mixtures thereof (i.e. mixtures of two or more of the aforementioned compounds).

In a twenty-sixth embodiment of the invention, which is a particular configuration of the twenty-second embodiment and all embodiments derived therefrom, the nitrogen compound used in step (I)(1) comprises ammonia gas, aqueous ammonia, ammonium salts (especially inorganic ammonium salts such as ammonium chloride and/or ammonium sulfate, preferably ammonium sulfate), urea or mixtures thereof (i.e. mixtures of two or more of the aforementioned compounds).

In a twenty-seventh embodiment of the invention, which is a particular configuration of the twenty-second embodiment and all embodiments derived therefrom, the microorganisms used in step (I)(1) comprise a species selected from the group consisting of *Escherichia coli, Pseudomonas putida, Corynebacterium glutamicum, Ashbya gossypii, Pichia pastoris, Hansenula polymorpha, Kluyveromyces marxianus, Yarrowia lipolytica, Zygosaccharomyces bailii* and *Saccharomyces cerevisiae*.

In a twenty-eighth embodiment of the invention, which can be combined with all embodiments, especially with the twenty-second embodiment and all embodiments derived therefrom, the aminobenzoic acid used for provision of the solution of aminobenzoic acid in aniline in step (I) comprises water in a proportion by mass based on the total mass of aminobenzoic acid and water in the range from 0.1% to 40%, preferably 1.0% to 20%, more preferably 2.0% to 10%.

In a twenty-ninth embodiment of the invention, which can be combined with all embodiments, step (III) is performed and comprises one of the following conversions:

(III)(1) acid-catalyzed reaction of aniline with formaldehyde to form di- and polyamines of the diphenylmethane series;
(III)(2) acid-catalyzed reaction of aniline with formaldehyde, followed by reaction with phosgene to form di- and polyisocyanates of the diphenylmethane series;
(III)(3) conversion of aniline to an azo compound.

The embodiments briefly outlined previously and further configurations of the invention are described in greater detail below. Various embodiments can be freely combined here with one another, unless the opposite is apparent to the person skilled in the art from the overall context.

Aminobenzoic acid occurs in three isomeric forms (ortho-, meta- and para-aminobenzoic acid). In principle, the process according to the invention can be applied to all three isomers, either in isomerically pure form or as mixtures of different isomers. For all the embodiments of the present invention, it is preferred that the aminobenzoic acid to be provided in step (I) comprises the ortho-isomer. More preferably, the aminobenzoic acid to be decarboxylated in step (I) comprises at least 50.0 mol %, most preferably at least 90.0 mol %, of the ortho isomer, based on the total molar amount of all aminobenzoic acid isomers present. The aminobenzoic acid to be decarboxylated in step (I) very exceptionally preferably consists of the ortho isomer in isomerically pure form (i.e. isomeric purity >99.0 mol %).

For performance of step (I), aminobenzoic acid and aniline are mixed. This is preferably accomplished in an industrial apparatus for mixing of two substances, a mixer, especially a stirred tank. The mixer may be operated batchwise or continuously. Irrespective of the type and mode of operation of the industrial apparatus used for mixing, the mixing is continued until the aminobenzoic acid has been completely or at least essentially completely dissolved. Depending on the proportion by mass of the aniline and the chosen temperature, this may have a different duration. The possibility of the presence of a small proportion of undissolved aminobenzoic acid is encompassed by the terminology according to the invention of "solution of aminobenzoic acid in aniline". A small proportion is understood here to mean that not more than 2% of the aminobenzoic acid is in undissolved form. Such a small proportion of solids is unproblematic since the continual conversion in the reactor from step (II) means that it rapidly goes into solution and is likewise converted to aniline.

In a preferred embodiment of the invention, the mixer is operated continuously, meaning that a stream of aminobenzoic acid—in solid form or as a suspension in preferably aqueous medium—and a stream of aniline are supplied continuously to the mixer, and a stream of aminobenzoic acid dissolved in aniline is withdrawn continuously from the mixer. This can be accomplished, for example, in a continuously operated stirred tank known to the person skilled in the art. The aminobenzoic acid/aniline stream withdrawn continuously from the mixer is fed continuously to the reactor from step (II).

Alternatively, it is possible to operate the mixer in step (I) batchwise. In this case, it is preferable to provide multiple, especially two, mixers that are connected in parallel and controllable independently of one another. This enables dissolution of aminobenzoic acid in aniline in a first mixer, while the dissolving operation is already completed in a second mixer and the resulting solution can be supplied to the reactor from step (II). While this solution is being supplied continuously to the reactor, the dissolving operation is completed in the first mixer, such that, after emptying of the second mixer, it is possible to switch to the first mixer and supply the solution produced therein to the reactor. The two mixers are thus alternately connected to the reactor from step (II), such that it can be charged continuously with aminobenzoic acid/aniline solution.

Irrespective of the exact configuration of step (I) in terms of process technology, it can be performed over a wide temperature range. What is essential is of course firstly that the aniline used as solvent is in liquid form, but secondly also that the temperature is not so high that the decarboxylation already begins during the dissolving operation. Therefore, step (I) can be performed at temperatures in the range from −6° C. to 120° C. Preference is given to temperatures in the range from 20° C. to 120° C., more preferably in the range from 30° C. to 120° C. What this means is that the temperature of the mixed aminobenzoic acid and aniline feedstocks is within these ranges, where the temperature during the dissolving operation may rise within the ranges mentioned.

It has been found to be useful to mix aminobenzoic acid and aniline first at temperatures in the range from −6° C. to 100° C., preferably in the range from 20° C. to 100° C., more preferably in the range from 30° C. to 100° C. This step does not require any inertization. However, the mixture thus prepared is inertized subsequently, i.e. blanketed with an inert gas atmosphere and preferably also stripped with an inert gas, and then heated in an inert gas atmosphere to a temperature in the range from >100° C. to 120° C. Suitable inert gases are carbon dioxide, noble gases such as helium or argon, and nitrogen. Preference is given to carbon dioxide or nitrogen, particular preference to nitrogen.

The solution provided in step (I) still has to be heated to the temperature envisaged for step (II). This is preferably accomplished by indirect heat transfer in a heat exchanger. It is advisable here to minimize the dwell time from entry of the solution into the heat exchanger until entry of preheated solution into the reactor from step (II) in order as far as possible to prevent commencement of the decarboxylation reaction even within the heat exchanger. Dwell times in the range from 0.1 s to 120 s have been found to be useful for this purpose.

With regard to the pressure to be observed in step (I), values in the range from 0.90 $bar_{(abs.)}$ to 3.0 $bar_{(abs.)}$, especially 1.0 $bar_{(abs.)}$ to 3.0 $bar_{(abs.)}$, are advisable, with measurement of the pressure in the gas space above the solution.

The aminobenzoic acid to be provided in step (I) can be obtained in principle in any way known to those skilled in the art. One option is the preparation of aminobenzoic acid by a chemical route. Preference is given to those methods that selectively afford the ortho isomer of aminobenzoic acid. One example of a suitable chemical method is the reaction of phthalimide with sodium hypochlorite. Phthalimide can itself be obtained from phthalic anhydride and ammonia. The whole process is well-known and is described, for example, in Lorz et al., *Phthalic Acid and Derivatives* in Ullmann's Encyclopedia of Industrial Chemistry, Volume 27, pp. 140-141, Weinheim, Wiley-VCH. An industrial process is likewise described in the patent literature; see, for example, DE 29 02 978 A1 and EP 0 004 635 A2.

Para-aminobenzoic acid can be prepared by a chemical route via the nitration of toluene with nitric acid, subsequent oxidation of the resulting para-nitrotoluene with oxygen to give para-nitrobenzoic acid and finally reduction with hydrazine to give para-aminobenzoic acid. The entire process is described, for example, in Maki et al., *Benzoic Acid and Derivatives* in Ullmann's Encyclopedia of Industrial Chemistry, Volume 5, pp. 338 ff., Weinheim, Wiley-VCH and in O. Kamm et al., *p-Nitrobenzoic acid* in Organic Syntheses, Volume 1, 1941, pp. 392 ff.

The preparation of meta-aminobenzoic acid is accomplished, for example, starting from methyl benzoate. Methyl meta-nitrobenzoate is obtained by nitrating methyl benzoate with nitric acid. This methyl ester is subsequently saponified with aqueous sodium hydroxide solution. Meta-nitrobenzoic acid is obtained after neutralization with hydrochloric acid, which is finally reduced with hydrazine to afford meta-aminobenzoic acid. The method is described, for example, in Maki et al., *Benzoic Acid and Derivatives* in Ullmann's Encyclopedia of Industrial Chemistry, Volume 5, pp. 338 ff., Weinheim, Wiley-VCH, in Kamm et al., *Methyl m-nitrobenzoate* in Organic Syntheses, Volume 1, 1941, pp. 372 ff. and in Kamm et al., *m-Nitrobenzoic acid* in Organic Syntheses, Volume 1, 1941, pp. 391 ff.

According to the invention, however, it is preferable to prepare the aminobenzoic acid required for performance of step (I) by a fermentative process. In this embodiment of the invention, the providing of the solution of aminobenzoic acid in aniline in step (I) preferably comprises the following partial steps:

(I)(1) fermenting a raw material comprising at least
    a fermentable carbon compound and
    a nitrogen compound,
      in a fermentation reactor using microorganisms to obtain an aminobenzoate- and/or aminobenzoic acid-containing fermentation broth,
      obtaining aminobenzoic acid from the fermentation broth;
    and
(I)(2) dissolving the aminobenzoic acid obtained from the fermentation broth in step (I)(1) in aniline.

Step (I)(1) of this embodiment of the process according to the invention can be performed by any fermentation method which is known from the prior art and is suitable for the preparation of aminobenzoic acid.

Depending on the pH at which the fermentation is performed, aminobenzoic acid is obtained in step (I)(1) not in electronically uncharged form, but as aminobenzoate for example (although this is immaterial in respect of the type of isomer formed). In the context of this invention, in connection with step (I)(1), for reasons of linguistic simplicity, reference is made regularly to aminobenzoic acid, which should be understood to include the cationic [i.e. diprotonated], anionic [i.e. deprotonated] and uncharged [i.e. electronically neutral] form of aminobenzoic acid. However, when it is evident from the constraints of a specifically outlined embodiment that the deprotonated form is formed for example, this is referred to as aminobenzoate.

A fermentable carbon compound in the context of this embodiment of the present invention is understood to mean any organic compound or mixture of organic compounds that can be used to produce aminobenzoic acid by the recombinant cells of the microorganism used. The production of aminobenzoic acid can take place here in the presence or in the absence of oxygen. Preference is given here to those fermentable carbon compounds which can additionally serve as energy and carbon source for the growth of the recombinant cells of the microorganism used. Particularly suitable are starch hydrolysate, sugarcane juice, sugarbeet juice and hydrolyzates of lignocellulosic raw materials, and mixtures thereof (i.e. mixtures of two or more of the aforementioned compounds). Likewise suitable are glycerol and C1 compounds, especially carbon monoxide. Useful nitrogen compounds suitable for step (I)(1) especially include ammonia gas, aqueous ammonia, ammonium salts (especially inorganic ammonium salts such as ammonium chloride and/or ammonium sulfate, preferably ammonium sulfate), urea or mixtures thereof (i.e. mixtures of two or more of the aforementioned compounds).

Preferred microorganisms for the performance of step (I-0) are bacteria or fungi, especially yeasts. Particular preference is given here to microorganisms of a species selected from the group consisting of *Escherichia coli, Pseudomonas putida, Corynebacterium glutamicum, Ashbya gossypii, Pichia pastoris, Hansenula polymorpha, Kluyveromyces marxianus, Yarrowia lipolytica, Zygosaccharomyces bailii* and *Saccharomyces cerevisiae*. The microorganisms used in step (I)(1) especially preferably consist solely of representatives of exactly one of these species, with very exceptional preference for *Corynebacterium glutamicum* ATTC 13032. The pH to be maintained in the fermentation is guided by the microorganism used. Microorganisms such as *Corynebacterium glutamicum, Pseudomonas putida* or *Escherichia coli* are preferably cultured at neutral pH (i.e. at a pH in the range from 6.0 to 8.0). Microorganisms such as *Saccharomyces cerevisiae*, by contrast, are preferably cultured in acidic medium (i.e. at a pH in the range from 3.0 to 6.0).

In each case, the microorganism from step (I)(1) is preferably selected such that the ortho isomer of aminobenzoic acid is formed in the fermentation.

In a preferred configuration of the invention, bacteria are used as microorganisms. In this connection, reference is made in particular to patent applications WO 2015/124686 A1 and WO 2015/124687 A1, which describe a fermentation usable according to the invention with use of bacteria (see, for example, WO 2015/124687 A1, (i) page 15, line 8 to page 16, line 30, (ii) example 1 (page 29, lines 4 to 26), (iii) example 3 (especially page 34, lines 10 to 18), (iv) example 4 (especially page 55, lines 9 to 31). In particular, bacteria are used which are capable of converting a fermentable carbon compound to aminobenzoic acid in the presence of a suitable nitrogen source without the aminobenzoic acid thus formed being consumed straight away in intracellular biochemical processes, with the result that aminobenzoic acid is enriched in the cell and ultimately passes into the fermentation broth.

In another preferred configuration of the invention, yeasts are used as microorganisms. Reference is made here in particular to international patent application WO 2017/102853 A1. In particular, yeast cells are used which are capable of converting a fermentable carbon compound to aminobenzoic acid in the presence of a suitable nitrogen source without the aminobenzoic acid thus formed being consumed straight away in intracellular biochemical processes, with the result that aminobenzoic acid is enriched in the cell and ultimately passes into the fermentation broth.

In order to obtain a bacterium of this kind or a yeast of this kind, two routes are available in principle, which may also be combined in a preferred configuration:

(i) The enzymatic reactions in the aminobenzoic acid metabolic pathway of the bacterial cell or yeast cell can be increased such that aminobenzoic acid is produced more rapidly than it is consumed.
(ii) The conversion reactions which convert aminobenzoic acid to further metabolites or products (e.g. tryptophan) can be reduced or switched off, with the result that even the rate of aminobenzoic acid formation in wild-type strains is sufficient to lead to an enrichment of aminobenzoic acid in the cell.

Methods for obtaining bacteria or yeast cells with the properties specified above are known from the prior art. Suitable bacteria or yeast cells can be identified, for example, by screening for mutants which secrete aminobenzoic acid into the surrounding medium. However, preference is given to the specific modification of key enzymes by means of genetic engineering methods. Using customary genetic engineering methods, gene expression and enzyme activity can be enhanced, reduced or even completely suppressed as desired. Recombinant strains are the result.

More preferably, the bacteria or yeast cells which are capable of converting a fermentable carbon compound to aminobenzoic acid in the presence of a nitrogen-containing compound contain a modification to the anthranilate phosphoribosyltransferase activity, which decreases said enzyme activity. As a result of said modification, the conversion of ortho-aminobenzoate to N-(5-phospho-D-ribosyl)anthranilate is reduced or completely suppressed. This causes enrichment of aminobenzoic acid in the cell. The expression "anthranilate phosphoribosyltransferase activity" refers here to an enzyme activity which catalyzes the conversion of ortho-aminobenzoate into N-(5-phospho-D-ribosyl)anthranilate.

In yeasts, anthranilate phosphoribosyltransferase activity is genetically encoded by the native gene TRP4 (YDR354W). In the bacterium *Corynebacterium glutamicum*, anthranilate phosphoribosyltransferase activity is encoded by the trpD gene (cg3361, Cgl3032, NCgl2929). In the case of *Pseudomonas putida*, the encoding is effected via the trpD gene (PP_0421) within the trpDC operon.

The described decrease in anthranilate phosphoribosyltransferase activity can be achieved in principle in three ways:
(i) The regulation of the expression of the gene for anthranilate phosphoribosyltransferase activity can be modified such that the transcription of the gene or subsequent translation is reduced or suppressed.
(ii) The nucleic acid sequence of the gene for anthranilate phosphoribosyltransferase activity can be modified such that the enzyme which is encoded by the modified gene has a lower specific activity.
(iii) The native gene for anthranilate phosphoribosyltransferase activity can be replaced with a different gene which originates from a different organism and encodes an enzyme having a specific anthranilate phosphoribosyltransferase activity lower than that of the native genes mentioned above (e.g. TRP4, trpD or trpDC).

Irrespective of which microorganism is used, the fermentation broth at the start of the fermentation in step (I)(1) comprises recombinant cells of the microorganism used and at least one fermentable carbon compound (and at least one nitrogen compound as nitrogen source). The fermentation broth preferably also comprises further constituents selected from the group consisting of buffer systems, inorganic nutrients, amino acids, vitamins and further organic compounds which are required for the growth or maintenance metabolism of the recombinant cells. The fermentation broth is water-based. After the fermentation process has been started, the fermentation broth also comprises aminobenzoic acid, the target fermentation product.

Step (I)(1) preferably also comprises a workup of the resulting fermentation broth. Said workup preferably comprises the following steps:
(α) separating the microorganism from the fermentation broth
and/or
(β) decolorizing the fermentation broth or, in the case of performance of step (α), the fermentation broth depleted of microorganisms obtained in step (α).

Separating the microorganism from the fermentation broth in step (α) is known per se from the prior art and is effected in the context of the present invention particularly by filtration, settling, separation in hydrocyclones or centrifugation. One possible configuration of this step is described in WO 2015/124686 A1 and WO 2015/124687 A1. Reference is made here in particular to WO 2015/124687 A1, page 15, line 8 to page 15, line 17.

Irrespective of whether or not the microorganism is separated off, step (I)(1) may, if required, comprise a step (β) for decolorizing the fermentation broth or the microorganism-depleted fermentation broth. This step (β) is preferably performed in such a way that fermentation broth or fermentation broth depleted of microorganisms is passed through a column with solid packing in order to remove dyes by means of adsorption. A possible solid phase used may, for example, be kieselguhr or ion exchanger packings. Step (β) is preferably performed when the fermentation broth or the microorganism-depleted fermentation broth from step (α) contains colored substances of the kind that could disrupt the step of obtaining the aminobenzoic acid from the fermentation broth.

The step of obtaining the aminobenzoic acid from the fermentation broth optionally treated according to step (α) and/or step (β) may have a different configuration depending on the pH of the fermentation broth obtained.

In the majority of cases, the fermentation broth after step (I)(1) is basic to neutral or slightly acidic at most (pH>4.7), and the aminobenzoic acid is consequently in the form of its aminobenzoate anion. In these cases, it is preferable to treat the fermentation broth with acid, especially with hydrochloric acid, sulfuric acid and/or phosphoric acid, in order to convert the anion to the electronically uncharged form. The acid is especially added until the pH of the resulting mixture is in the range from 3.0 to 4.7, preferably in the range from 3.2 to 3.7 (especially in the case of meta- and para-aminobenzoic acid), more preferably in the range from 3.4 to 3.6 (especially in the case of ortho-aminobenzoic acid). Aminobenzoic acid is then predominantly to completely in the electronically uncharged form and, owing to the low water solubility thereof, precipitates out apart from a small proportion attributable to a certain residual solubility, and can easily be separated from the supernatant fermentation broth, especially by filtration or centrifugation. Filtration can be carried out at reduced pressure, atmospheric pressure or elevated pressure. Centrifugation can be carried out using commercial centrifuges. It is also possible to leave the suspension obtained in the acid treatment standing until the precipitated crystals of aminobenzoic acid settle out and to then decant the supernatant mother liquor or filter it off with suction.

Should the fermentation broth after step (I)(1) be strongly acidic (pH<3.0), a pH in the aforementioned ranges is ensured by adding base (preferably aqueous sodium hydroxide solution, lime). If the pH of the fermentation broth after step (I)(1), optionally after performance of step (α) and/or step (β), by contrast, is in the range from 3.0 to 4.0, as can be the case when using yeasts as microorganisms, neither acid nor base is added in a preferred embodiment, but rather the fermentation broth is processed further directly without further pH adjustment. In this case, it is to be expected that crystals of aminobenzoic acid will spontaneously precipitate and can be directly separated off. With regard to the methods employable for this purpose, the statements made above for the acid treatment are applicable.

Any necessary separation of solid aminobenzoic acid and solid microorganisms present in aqueous solution is best accomplished through centrifugation. This is true of all embodiments of the present invention in which such a separation is required.

The aminobenzoic acid obtained in one of the ways described above can be processed further prior to the performance of step (I)(2). Preference is given to scrubbing with aqueous wash media, especially water. In order to avoid yield losses, the pH of the aqueous wash medium can be adjusted to the same pH as after the end of addition of acid (or in the case of yeasts: addition of base); it is thus possible in this embodiment to wash with a diluted acid rather than with water. Suitable acids for this purpose are the acids mentioned above in connection with the acid treatment.

In a preferred embodiment, step (I)(1) is performed continuously, i.e. the reactants are fed continuously to the fermentation reactor and the product is withdrawn continuously from the fermentation reactor. In a continuous process regime, the microorganism is discharged, under certain circumstances, with the product stream; however, since the microorganism generally reproduces itself, feeding fresh microorganism is generally unnecessary (but can of course be done if required). Cell retention to avoid discharge of microorganism is also possible.

In another preferred embodiment, step (I)(1) is performed in a batchwise process regime (called "batchwise mode"). In one variant of the batchwise mode of operation (called "fed-batch mode"), the reactants are fed continuously to the fermentation reactor for as long as the reactor volume allows it without products being withdrawn from the reactor. The reaction is stopped after addition of the maximum possible amount of reactants and the product mixture is withdrawn from the fermentation reactor.

Irrespective of the exact mode of operation, the fermentation reactor preferably comprises devices for measuring important process parameters such as temperature, pH of the fermentation broth, concentration of substrate and product, dissolved oxygen content, and cell density of the fermentation broth. In particular, the fermentation reactor preferably comprises devices for adjusting at least one (preferably all) of the aforementioned process parameters.

Suitable fermentation reactors are stirred tanks, membrane reactors, plug flow reactors or loop reactors (see for example Bioprozesstechnik, Horst Chmiel, ISBN-10: 3827424763, Spektrum Akademischer Verlag). Particularly preferred for both aerobic and anaerobic fermentations are stirred tank reactors and loop reactors (particularly airlift reactors in which circulation of the liquid in the reactor is achieved by sparging).

In a particularly preferred embodiment, step (I)(1) is performed in the presence of a calcium salt, such that aminobenzoic acid precipitates out in the form of its sparingly soluble calcium salt $Ca(OOC-C_6H_4-NH_2)_2$. Such a process is described in as yet unpublished European patent application EP18176433.3 and comprises the following further steps:

(i) converting calcium aminobenzoate to a water-soluble form by adding an aqueous phase containing water-soluble cations that form aminobenzoate salts (especially lithium, sodium, potassium and/or ammonium cations, preferably ammonium cations) and anions that form water-insoluble calcium salts (especially carbonate and/or hydrogen carbonate anions);
(ii) separating off an aqueous solution of aminobenzoate;
(iii) introducing carbon dioxide at a pressure of not less than 1.50 $bar_{(abs.)}$ into the aqueous solution of aminobenzoate separated off, so as to form a suspension containing aminobenzoic acid in an aqueous solution;
(iv) isolating the aminobenzoic acid separated out, comprising lowering the pressure with release of carbon dioxide to obtain a carbon dioxide-depleted aqueous solution that has been freed of aminobenzoic acid separated out;
(v) using the resultant aqueous solution that has been depleted of carbon dioxide and freed of aminobenzoic acid separated out as constituent, optionally sole constituent, of the aqueous phase added in step (i).

Irrespective of the microorganism used and the carbon and nitrogen source chosen, the calcium salt to be used in step (I)(1) is preferably selected from calcium carbonate, calcium hydrogen carbonate, calcium hydroxide, calcium oxide or mixtures of two or more of the aforementioned compounds. Especially preferred is the use of a mixture of calcium carbonate and calcium hydroxide. A suspension of calcium carbonate in water—since calcium carbonate goes partly into solution and the dissolved carbonate ions form hydrogencarbonate and hydroxide ions with water—always contains also proportions of calcium hydroxide and is therefore encompassed by the wording "mixture of calcium carbonate and calcium hydroxide". The use of such calcium salts has the advantage that the addition of further bases, for example sodium hydroxide (see, for instance, the processes described in WO 2015/124686 A1 and WO 2015/124687 A1), as buffer is required in a reduced amount at most, if at all. Calcium carbonate may be initially charged in the fermentation reactor in solid form. Addition as an aqueous suspension is also possible. Calcium oxide may in principle likewise be introduced into the fermentation reactor in solid form. If calcium oxide is available as calcium source, however, it is preferable first to quench it with water and hence convert it to calcium hydroxide. Calcium hydroxide and calcium hydrogencarbonate are preferably metered in in the form of aqueous solutions.

The aqueous fermentation solution remaining after the isolation of the calcium aminobenzoate has a pH of especially 4.0 or more, depending on the exact conditions of the fermentation. Since this aqueous fermentation solution can still contain proportions of dissolved aminobenzoate, it is advantageously possible to crystallize to aminobenzoic acid out of it by addition of acid, and to isolate the crystallized aminobenzoic acid, leaving a mother liquor depleted of aminobenzoic acid. With regard to suitable acids and pH values, reference is made to the above remarks that are also applicable here.

Irrespective of the exact configuration of the fermentation and the step of obtaining the aminobenzoic acid, the latter is always in aqueous form when obtained by fermentation. It is preferable not to remove or at least not completely remove this water content, such that the aminobenzoic acid used for provision of the solution of aminobenzoic acid in aniline in step (I) comprises water in a proportion by mass based on the total mass of aminobenzoic acid and water in the range from 0.1% to 40%, preferably 1.0% to 20%, more preferably 2.0% to 10%. This has the advantage that there is no need for complete drying of water-moist aminobenzoic acid, which is very energy- and time-consuming and requires specific technical apparatus. It is possible to dispense with this complete drying, which distinctly reduces the time taken and costs, and the technical complexity of the overall process.

The solution of aminobenzoic acid in aniline provided in the manner described above is subjected to decarboxylation conditions in step (II). According to the invention, high temperatures are required for this purpose, i.e. temperatures in the range from 165° C. to 500° C. Preferred temperatures are in the range from 185° C. to 450° C., more preferably in the range from 205° C. to 425° C., even more preferably in the range from 225° C. to 400° C., very exceptionally preferably in the range from 255° C. to 375° C. With regard to the process pressure, it is preferable to perform the thermal decarboxylating in step (II) at pressure values in the range from 4.0 $bar_{(abs.)}$ to 30 $bar_{(abs.)}$, preferably 5.0 $bar_{(abs.)}$ to 20 $bar_{(abs.)}$, more preferably 6.0 $bar_{(abs.)}$ to 10 $bar_{(abs.)}$ and most preferably 7.0 $bar_{(abs.)}$ to 9.0 $bar_{(abs.)}$. This means the pressure in the gas space of the reactor above the liquid level (the pressure at the top of the reactor in the case of upright reactors in column form).

For most applications, it is preferable to purify aniline formed in the decarboxylation prior to further use thereof, especially by distillation. In this case, step (II) of the present invention comprises a first partial step (II)(1), the thermal decarboxylation, which is followed by a second partial step (II)(2) in which aniline formed in partial step (II)(1) is purified. This purification can be effected by processes familiar to the person skilled in the art. In particular, the purification includes at least one distillation step, which may be preceded by removal of water by phase separation. The purification may likewise include a base treatment for removing acidic impurities before, during or after the distillation step. Suitable configurations are described, for example, in EP-A-1 845 079, EP-A-1 845 080, EP-A-2 263 997 and EP-A-2 028 176. (These documents are concerned with the purification of aniline which has been obtained by hydrogenation of nitrobenzene; the described steps for purifying the crude aniline are, however, also applicable to aniline produced in other ways.)

The aniline to be used for the dissolving of the aminobenzoic acid in step (I) may be taken from the aniline formed in partial step (II)(1), i.e. the aminobenzoic acid is dissolved in crude aniline in step (I). The use of crude aniline as solvent for aminobenzoic acid to be decarboxylated is already known from international patent application WO 2018/002088 A1. If the catalyst extraneous to the system which is required therein is dispensed with and the ranges of values required according to the invention for temperature and proportion by mass of aniline are observed, it is advantageously possible to make use of the procedure in terms of chemical engineering described therein.

However, it is likewise possible to take the aniline to be used for the dissolution of the aminobenzoic acid in step (I) from the aniline formed in partial step (I)(2), i.e. to use pure aniline for the dissolving of the aminobenzoic acid in step (I). This is especially preferable if the crude aniline should contain impurities that impair the decarboxylation to a problematic degree. In addition, it is of course also possible to use a mixture of crude and pure aniline, i.e. aniline from partial steps (II)(1) and (II)(2), for dissolution of the aminobenzoic acid in step (I), for instance in order to dilute such impurities into an uncritical range.

If crude aniline is to be used for the performance of step (I), it is preferable to divide the aniline formed in partial step (II)(1) into two streams in a mass ratio in the range from 9.0:1 to 1:9.0, one of which is supplied to the purification from partial step (II)(2) and the other used to provide the solution in step (I).

During the thermal decarboxylation, gaseous carbon dioxide is formed. It is preferable to withdraw this continuously from the reactor used in step (II). There is always also entrainment here of a portion of the aniline in gaseous form, such that it is advisable, for avoidance of product losses, to guide the discharged gas stream containing carbon dioxide and gaseous aniline through a condenser in which gaseous aniline is liquefied and from which carbon dioxide is discharged in gaseous form, with supply of liquid aniline obtained in the condenser to partial step (II)(1) and/or to partial step (II)(2). It is preferable to adjust the pressure of the carbon dioxide discharged from the condenser in gaseous form to a value in the range from 1.0 $bar_{(abs.)}$ to 30 $bar_{(abs.)}$, preferably 2.0 $bar_{(abs.)}$ to 20 $bar_{(abs.)}$, more preferably 3.0 $bar_{(abs.)}$ to 10 $bar_{(abs.)}$ and most preferably 3.0 $bar_{(abs.)}$ to 9.0 $bar_{(abs.)}$. This can be achieved in a simple manner by means of closed-loop control circuits known to the person skilled in the art.

Suitable reactors for the performance of step (II) are in principle reactor types that are customary in chemical engineering and are familiar to the person skilled in the art. The expression "in a reactor" here, according to the invention, also includes embodiments in which two or more reactors of a reactor cascade are connected in series, i.e. the liquid product discharge from one reactor flows into the next reactor for further completion of the conversion. It is possible to feed the solution of aminobenzoic acid in aniline provided in step (I) solely into the first reactor of a reactor cascade. However, it is likewise possible to feed the solution provided in step (I) into each reactor of a reactor cascade.

In one embodiment of the invention, the reactor used in step (II) is a continuously operated tubular reactor.

In another embodiment of the invention, the reactor used in step (II) is a continuously operated bubble column reactor. The latter preferably has internals, especially perforated plates that subdivide the bubble column reactor into compartments. Bubble columns are apparatuses in which gas in the form of bubbles comes into contact with a continuously flowing liquid. In the context of the present invention, the continuously flowing liquid is the solution of aminobenzoic acid in aniline that flows, preferably from the bottom upward, through an upright reactor in column form. The gas is the carbon dioxide formed (and any inert gas additionally supplied). A liquid-gas separation takes place at the top of the reactor; liquid aniline separates from carbon dioxide gas (optionally containing proportions of entrained gaseous aniline).

In all embodiments, it is preferable to perform step (II) with exclusion of oxygen. Suitable gases for inertization of the reactor are inert gases such as nitrogen, carbon dioxide, or noble gases such as helium or argon. Preference is given to nitrogen or carbon dioxide, particular preference to nitrogen.

The procedure according to the invention for performing the decarboxylation in a reaction medium consisting of aniline in significant proportions and comprising no catalyst extraneous to the system has various advantages over the methods known from the literature:

Dispensing with catalysts extraneous to the system considerably reduces the complexity of the process, as elucidated in detail further up;

Reduced costs, since no costs arise for acquisition and regeneration of catalysts;

Simplified purification of the aniline product since no catalyst has to be removed.

The aniline obtained according to the invention is preferably converted further to an aniline conversion product, i.e. step (III) is preferably performed. Selected further reactions of the aniline obtained in step (III) are:

(III)(1) acid-catalyzed reaction of aniline with formaldehyde to form di- and polyamines of the diphenylmethane series;

(III)(2) acid-catalyzed reaction of aniline with formaldehyde, followed by reaction with phosgene to form di- and polyisocyanates of the diphenylmethane series;

(III)(3) conversion of aniline to an azo compound.

The further reaction of aniline with formaldehyde to give di- and polyamines of the diphenylmethane series (III)(1) is known per se and may be performed by any prior art method. The continuous or partially discontinuous preparation of di- and polyamines of the diphenylmethane series from aniline and formaldehyde is, for example, disclosed in EP 1 616 890 A1, U.S. Pat. No. 5,286,760, EP-A-451442 and WO-A-99/40059. The reaction is effected under acid catalysis. Suitable as acidic catalyst is preferably hydrochloric acid.

Further reaction of the di- and polyamines of the diphenylmethane series that are thus obtained with phosgene to give di- and polyisocyanates of the diphenylmethane series (III)(2) is also known per se and may be performed by any prior art method. Suitable processes are described, for example, in EP 2 077 150 B1, EP 1 616 857 A1, EP 1 873 142 A1, and EP 0 314 985 B1.

The conversion of the aniline obtained according to the invention to azo compounds, especially to azo dyes (III)(3) may be effected by any prior art method. Reference may be made by way of example to the known preparation of aniline yellow (para-aminoazobenzene; CAS 493-5-7) or indigo (2,2'-bis(2,3-dihydro-3-oxomethylidene); CAS 482-89-3) (Per Wiklund et al., *Current Organic Synthesis*, 2006, 3, 379-402).

Examples

Chemicals Used:

2-Aminobenzoic acid, CAS 118-92-3 (short form hereinafter: oAB): purity ≥98%, Sigma-Aldrich Chemie GmbH.

Aniline, CAS 62-53-3 (short form hereinafter: ANL): purity ≥99%, Sigma-Aldrich Chemie GmbH.

Demineralized water (short form hereinafter: $H_2O$): "HPLC Grade" purity, Sigma-Aldrich Chemie GmbH.

2-Amino-N-phenylbenzamide, CAS 4424-17-3 (short form hereinafter: amide): purity ≥98%, Sigma-Aldrich Chemie GmbH.

Methanol, CAS 67-56-1 (short form hereinafter: MeOH): "HPLC Grade" purity, Sigma-Aldrich Chemie GmbH.

Phosphoric acid "ACS reagent", CAS 7664-38-2 (short form hereinafter: $H_3PO_4$): purity ≥85%, Sigma-Aldrich Chemie GmbH.

Catalyst (for Comparative Examples):

CBV 600 (CAS 1318-02-1), Zeolyst International, Inc., surface area 660 $m^2/g$, pore size 2.43 nm, Si/Al ratio 2.5. The catalyst was calcined prior to use at 300° C. in air for 3 h.

General Experimental Method for Experiments with Catalyst (Comparative Examples):

An initial charge of 1.33 g of oAB, 2 mL of ANL and 0.08 g of catalyst in a 10 mL pressure reactor was purged with argon as protective gas, and the reactor was closed. Subsequently, argon was injected to a pressure of 3 bar, the mixture was stirred at 800 rpm for 2 min and the pressure was dropped to 1 bar. This operation was repeated 3 times before the reactor was brought to the reaction temperature (see table 1). After the appropriate reaction time (see table 1), the pressure reactor was cooled down from reaction temperature to room temperature in an ice bath, and the pressure was subsequently dropped. The catalyst was separated from the reaction mixture by means of centrifugation (5 min, 5000 rpm). The composition of the liquid supernatant was analyzed by means of HPLC analysis (for data see table 1).

General Experimental Method for Experiments without Catalyst (Working Examples):

The reaction procedure was analogous to "General experimental method for experiments with catalyst", except that no catalyst was employed and method steps relating to the catalyst are thus omitted.

HPLC Analyses:

Quantitative analysis of oAB, ANL and amide in the reaction mixture was accomplished by high-performance liquid chromatography (HPLC) analysis. For HPLC analysis, a setup from Agilent was used with UV detection (DAD, measured at 254.4 nm). For separation, a column from Agilent (Eclipse XDB-C18; 5 m; 4.6×150 mm) was used. The element used was a mixture of MeOH and $H_2O$ (ratio 40:60, pH 3 established with $H_3PO_4$) at a flow rate of 0.7 mL/min. The temperature of the column oven was 25° C. The sample was diluted in MeOH at a ratio of 1:10; the injection volume was 1 µL. The retention times of the individual ANL, oAB and amide components were:

ANL=2.87 min;
oAB=6.00 min;
amide=18.67 min.

The peak areas are converted to area percent (A %). The quantification of the individual components in percent by mass (% by mass) based on the reaction mixture was enabled by calibration with pure substances beforehand. Tabulated in table 1 are all product compositions for the working and comparative examples for a given reaction time.

Determination of Reaction Rates:

The reaction rate was determined by ascertaining the rate constant k (in $min^{-1}$) of the conversion of oAB. The basis used was pseudo-first-order conversion kinetics based on oAB, and the conversion of oAB was determined experimentally for different reaction times. For calculation of k, the natural logarithms of the relative oAB concentrations were plotted against reaction time (in min) and subjected to a linear fit. The slope of the linear equation thus obtained corresponds to k in $min^{-1}$. Tabulated in table 1 are all k values for the working and comparative examples.

TABLE 1

Working examples (without catalyst) and comparative examples (with catalyst)

| # | Note | T [° C.] | k [$min^{-1}$] | after [min] | oAB [% by mass] | ANL [% by mass] | Amide [% by mass] | ΣA % of these components in HPLC |
|---|---|---|---|---|---|---|---|---|
| 1 | without catalyst | 200 | 0.053 | 60 | 10.9 | 88.9 | 0.2 | 100 |
| 2 | | 230 | 0.091 | 60 | 3.2 | 96.5 | 0.3 | 100 |
| 3 | | 250 | 0.118 | 30 | 0.8 | 98.8 | 0.4 | 100 |
| 4 | | 270 | 0.143 | 30 | 0.4 | 99.2 | 0.4 | 100 |
| 5 | without catalyst | 200 | 0.032 | 60 | 14.1 | 85.7 | 0.3 | 100 |
| 6 | with 5% by mass of $H_2O$ based on oAB | 225 | 0.052 | 60 | 3.9 | 95.7 | 0.3 | 100 |
| 7 | without catalyst | 200 | 0.031 | 60 | 14.1 | 85.7 | 0.2 | 100 |
| 8 | with 30% by mass of $H_2O$ based on oAB | 225 | 0.054 | 60 | 3.6 | 96.1 | 0.4 | 100 |
| 9 | with catalyst | 200 | 0.052 | 60 | 2 | n.d. | n.d. | n.d. |
| 10 | with catalyst with 5% by mass of $H_2O$ based on oAB | 200 | 0.030 | 60 | 1.4 | 98 | 0.6 | >99 |
| 11 | with catalyst with 30% by mass of $H_2O$ | 200 | 0.041 | 60 | 0.9 | 99 | 0.1 | 100 |

TABLE 1-continued

Working examples (without catalyst) and comparative examples (with catalyst)

| # | Note | T [° C.] | k [min$^{-1}$] | oAB after [min] | ANL [% by mass] | Amide [% by mass] | ΣA % of these components in HPLC |
|---|------|----------|----------------|-----------------|-----------------|-------------------|----------------------------------|
|   | based on oAB | | | | | | |

Elucidation of abbreviations: n.d. = not determined, ΣA % = sum total of the area percentages (of the three components oAB, ANL and amide)

The invention claimed is:

1. A process for preparing aniline, comprising:
   (I) providing a solution of aminobenzoic acid in aniline, wherein aniline is present in the solution in an amount of 20% to 85% by mass, based on the total mass of aminobenzoic acid and aniline; and
   (II) converting aminobenzoic acid in the solution provided in step (I) to aniline in a reactor by thermal decarboxylation at a temperature of 165° C. to 500° C. without the presence of any catalyst extraneous to the system.

2. The process as claimed in claim 1, in which step (I) is performed by mixing aminobenzoic acid and aniline in a batchwise or continuous mixer.

3. The process as claimed in claim 2, in which the mixer and the reactor are operated continuously.

4. The process as claimed in claim 2, in which step (I) is performed using multiple batchwise mixers connected in parallel and the reactor is operated continuously, wherein, at any time in the continuous operation of the reactor, the solution of the aminobenzoic acid from one of the mixers is introduced into the reactor, while the mixing of the aminobenzoic acid into aniline is proceeding in another of the mixers.

5. The process as claimed in claim 1, in which the thermal decarboxylation of the aminobenzoic acid is a first partial step (II)(1) of step (II), which is followed by a second partial step (II)(2) in which aniline formed in partial step (II)(1) is purified.

6. The process as claimed in claim 5, in which the aniline used in step (I) is taken
   from the aniline formed in partial step (II)(1),
   from the aniline purified in partial step (II)(2)
   or
   from the aniline formed in partial step (II)(1) and from the aniline purified in partial step (II)(2).

7. The process as claimed in claim 1, in which, in step (I), aminobenzoic acid is dissolved in aniline at a temperature of −6° C. to 120° C.

8. The process as claimed in claim 7, in which aminobenzoic acid and aniline are first mixed at a temperature of −6° C. to 100° C. and then heated in an inert gas atmosphere to a temperature of >100° C. to 120° C.

9. The process as claimed in claim 1, in which the thermal decarboxylation in step (II) is performed at a pressure of 4.0 bar$_{(abs.)}$ to 30 bar$_{(abs.)}$.

10. The process as claimed in claim 5, in which a liquid, aniline-containing stream and a gaseous, carbon dioxide- and gaseous aniline-containing stream are taken continuously from the reactor, wherein the gaseous stream passes through a condenser in which gaseous aniline is liquefied and from which carbon dioxide is discharged in gaseous form, wherein liquid aniline obtained in the condenser is fed to partial step (II)(1) and/or to partial step (II)(2).

11. The process as claimed in claim 1, in which the providing of the solution of aminobenzoic acid in aniline in step (I) comprises the chemical preparation of aminobenzoic acid.

12. The process as claimed in claim 1, in which the providing of the solution of aminobenzoic acid in aniline in step (I) comprises:
   (I)(1) fermenting a raw material comprising at least
      a fermentable carbon compound and
      a nitrogen compound,
      in a fermentation reactor using microorganisms to obtain an aminobenzoate- and/or aminobenzoic acid-containing fermentation broth,
   (I)(2) obtaining aminobenzoic acid from the fermentation broth;
   and
   (I)(3) dissolving the aminobenzoic acid obtained from the fermentation broth in step (I)(1) in aniline.

13. The process as claimed in claim 12, in which the microorganisms used in step (I)(1) comprises any one or more of *Escherichia coli*, *Pseudomonas putida*, *Corynebacterium glutamicum*, *Ashbya gossypii*, *Pichia pastoris*, *Hansenula polymorpha*, *Kluyveromyces marxianus*, *Yarrowia lipolytica*, *Zygosaccharomyces bailii* and *Saccharomyces cerevisiae*.

14. The process as claimed in claim 1, in which the aminobenzoic acid used to provide the solution of aminobenzoic acid in aniline in step (I) comprises water in an amount of 0.1% to 40% by mass, based on the total mass of aminobenzoic acid and water.

* * * * *